United States Patent [19]

Johnson

[11] 4,365,637
[45] Dec. 28, 1982

[54] PERSPIRATION INDICATING ALARM FOR DIABETICS

[75] Inventor: Wilton C. Johnson, Hopkins, Minn.

[73] Assignee: Dia-Med, Inc., Hopkins, Minn.

[21] Appl. No.: 191,699

[22] Filed: Sep. 29, 1980

Related U.S. Application Data

[63] Continuation-in-part of Ser. No. 54,820, Jul. 5, 1979, abandoned.

[51] Int. Cl.³ ............................................. A61B 5/05
[52] U.S. Cl. .................................... 128/734; 128/644
[58] Field of Search ............................. 128/734–735, 128/639–644; 73/73; 324/61 R, 61 P, 65 R, 65 P; 340/573, 603–605

[56] References Cited

U.S. PATENT DOCUMENTS

| | | | |
|---|---|---|---|
| 3,382,434 | 5/1968 | Gibson, Jr. et al. | 128/734 |
| 3,580,239 | 5/1971 | Watanobe et al. | 128/639 X |
| 3,870,034 | 3/1975 | James | 128/734 |
| 3,901,214 | 8/1975 | Taafe | 128/734 |
| 3,924,606 | 12/1975 | Silva et al. | 128/734 |
| 3,954,100 | 5/1976 | Sem-Jacobsen | 128/639 |
| 4,082,087 | 4/1978 | Howson | 128/640 |
| 4,178,916 | 12/1979 | McNamara | 128/734 |

FOREIGN PATENT DOCUMENTS

| | | | |
|---|---|---|---|
| 2735603 | 2/1979 | Fed. Rep. of Germany | 128/734 |
| 2912349 | 10/1980 | Fed. Rep. of Germany | 128/734 |

Primary Examiner—Kyle L. Howell
Assistant Examiner—Francis J. Jaworski
Attorney, Agent, or Firm—Schroeder, Siegfried, Vidas, Steffey & Arrett

[57] ABSTRACT

A self-contained wearable device for use by diabetics to provide an audible indication of the onset of insulin shock. The device utilizes a sensor positioned to sense the buildup of perspiration on the skin of the user and an annunciator to provide an audible warning when the amount of perspiration on the skin of the wearer exceeds a predetermined threshold level. The distance between the sensor and the user's skin is adjustable to prevent false operation of the device due to changes in the resistance of the user's skin.

5 Claims, 6 Drawing Figures

4,365,637

PERSPIRATION INDICATING ALARM FOR DIABETICS

This application is a continuation-in-part of Ser. No. 54,820, July 5, 1979, abandoned.

DESCRIPTION

BACKGROUND OF THE INVENTION

This invention relates to a self-contained and wearable device for monitoring the amount of perspiration which is present on the skin of a user to detect the onset of insulin shock and provide and audible warning.

DESCRIPTION OF THE PRIOR ART

Management of patients with severe diabetes poses some difficult problems. In such diabetics, often referred to as "brittle" diabetics, there is a possibility that insulin shock will develop while the patient is sleeping, for example. In such instances, it is essential that the patient be wakened promptly so that necessary steps can be taken to avoid a complete onset of shock and possible coma. If the onset of diabetic shock is detected at a sufficiently early point, the ingestion of a small amount of food may be sufficient to reverse and totally control the reaction. If the patient is asleep and the condition remains undetected for any considerable period of time, the symptoms may become quite severe and require hospitalization to control.

A physiological condition which is indicative of the onset of diabetic shock is excessive sweating by the patient in the early stages. It is known to use electronic devices to detect the increase of the rate of perspiration characteristic of physiological conditions such as insulin reaction. U.S. Pat. No. 2,812,757, relates to a device for detecting an increase in the perspiration rate of a diabetic. That system utilizes a cloth-like tape with conductors therein which is placed beneath the bottom bed sheet of the patient's bed and extends across the bed. The increase in perspiration must soak through the bed sheet and wet the tape before triggering the alarm. A thyratron circuit is used in the arrangement to detect the change in resistance between conductors imbedded in the tape.

It is desired to provide a fast reacting self-contained wearable device to detect an increase in rate of perspiration at an early stage to warn of the onset of diabetic insulin reaction.

Further, it is desired to provide a portable physiological monitor energized by a self-contained power source such as a battery. When using batteries in such a monitor, it is desired to minimize the energy drain therefrom in order to extend their life. Thus, it is desired to only intermittently operate the active circuits in the sensor to minimize the current drain.

SUMMARY OF THE INVENTION

It is an object of this invention to provide a new and improved physiological monitor that may be worn by a patient to detect an increase in perspiration rate indicative of the onset of insulin reaction in a diabetic.

It is a further object to this invention to provide a new battery powered physiological monitor adapted to be energized by a self-contained power source such as a battery and, in particular, to reduce the energy drain upon the self-contained power source.

It is still a further object of this invention to provide a new and improved perspiration measuring system implemented by solid state circuitry designed to minimize the power drain upon the self-contained power source.

In accordance with these and other objects, this invention is directed toward a device for detecting the onset of insulin shock in a diabetic comprising a sensor constructed and arranged for application to the skin of a wearer, a detector connected to the sensor to provide an output when the amount of perspiration on the skin of the wearer exceeds a certain threshold level, and an annunciator connected to the detector to receive the output therefrom and provide an audible output indication.

BRIEF DESCRIPTION OF THE DRAWINGS

These and other objects and advantages of the invention will become more apparent by referring to the following detailed description of the accompanying drawings, in which.

DETAILED DESCRIPTION OF THE PREFERRED EMBODIMENT

Figure 1:
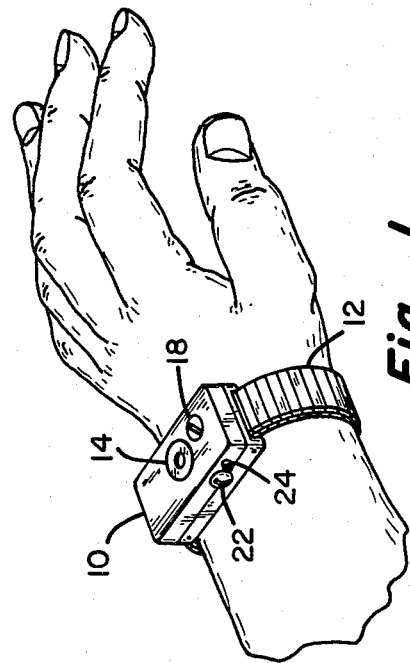
FIG. 1 is a pictorial view of the device being worn by a user.

With regard to the drawings, and in particular to FIG. 1, there is shown a perspiration detection device 10 which has a size and shape similar to a conventional wristwatch positioned on the wrist of a wearer, utilizing a conventional expansion wrist band 12. It would, of course, be possible to utilize the invention in other locations by positioning the detection device 10 utilizing other affixing means such as tape or elastic belts.

The top of the case of the device 10 includes an aperture for a sound transducer 14 which, in the preferred embodiment shown, is a commercially available miniature loudspeaker. The batteries 16 are conventional electric watch batteries which are positioned beneath a screw-in cover so that they can be readily accessed for testing and replacement.

The wiper of an adjustable resistor 20 is moved by the adjustment screw 22 in the side of the case of the detector device to provide a sensitivity adjustment as described below. A test switch 24 is used to test the operability of the device and the condition of the batteries as described below.

Figure 3:
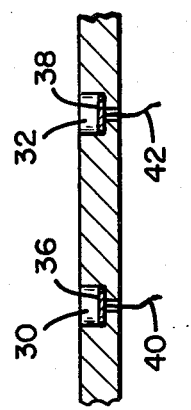
FIG. 3 is a partial section showing the detail of the back of the device.
Figure 2:
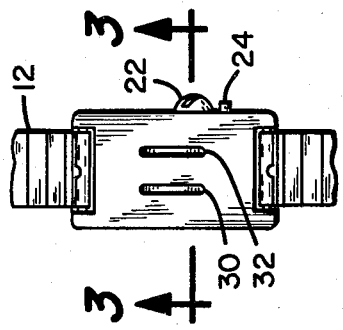
FIG. 2 is a plan view of the back of the device.
Figure 5:
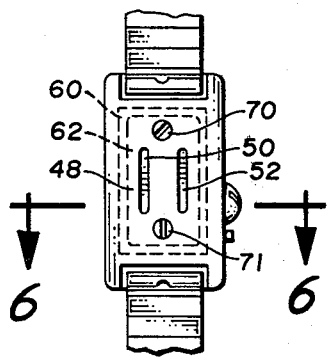
FIG. 5 is a plan view of the back of an alternate embodiment of the device.
Figure 6:
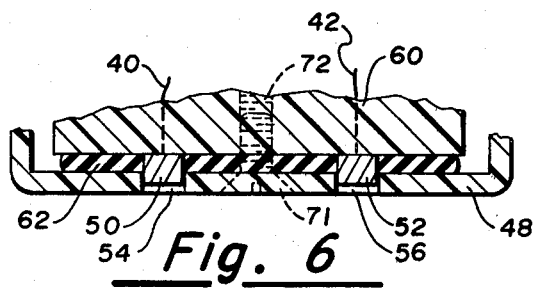
FIG. 6 is a partial section showing the detail of the adjustable sensor.

FIG. 2 shows the back of one form of the device 10. Positioned on the back of the device are a pair of slots 30 and 32 which are shown in further detail in the partial cross section of the bottom of the case of the device in FIG. 3. FIG. 3 shows that the slots 30 and 32 have electrodes 36 and 38 fixedly positioned within them. Suitable lead wires 40 and 42 connect the electrodes to the circuit shown in FIG. 4:

FIGS. 5 and 6 show another embodiment of the device employing electrodes which may be adjusted to vary their distance from the skin of the user. In this embodiment the electrodes are mounted on a substrate which is movable with respect to the back face of the case of the detector as adjusting screws 70 and 71 are rotated. The electrodes are adjustable between a position where they are substantially flush with the back of the case to a position where they are retracted approximately 0.16 cm.

FIG. 6 shows the details of the mounting of the adjustable electrode on substrate 60. Electrodes 50 and 52 project above the surface of the substrate. The substrate 60 is aligned with slots 30 and 32 in the back face 48 of the case. A rubber or other resilient mounting and bias means 62 is interposed between substrate 60 and the case. Adjustment of screws 70 and 71 in mounting holes 72 varies the distance between substrate 60 and the wall 48 of the case to alter the distance between the skin of the wearer and electrodes 50 and 52.

It is an important feature of the invention that the electrodes 36 and 38 are not positioned in direct contact with the patient's skin, but are offset somewhat. If the buildup of perspiration on the wrist of the wearer reaches a level indicative of an abnormal condition such as early diabetic shock, it comes into contact with electrodes 36 and 28. Because of its salinity, the layer of perspiration forms a low resistance path between conductors 40 and 42. The depth at which the electrodes 36 and 38 are set from the nonconductive back surface of the case of device 10 is selected such that the formation of beads of perspiration on the skin of the wearer make contact with the electrodes 36 and 38. The recess depth is in the preferred embodiment, approximately 1/16". Because the electrodes come into direct contact with the perspiration without being required to soak through bed sheets or other materials, the device may detect an increase in perspiration rate at a very early point.

Figure 4:
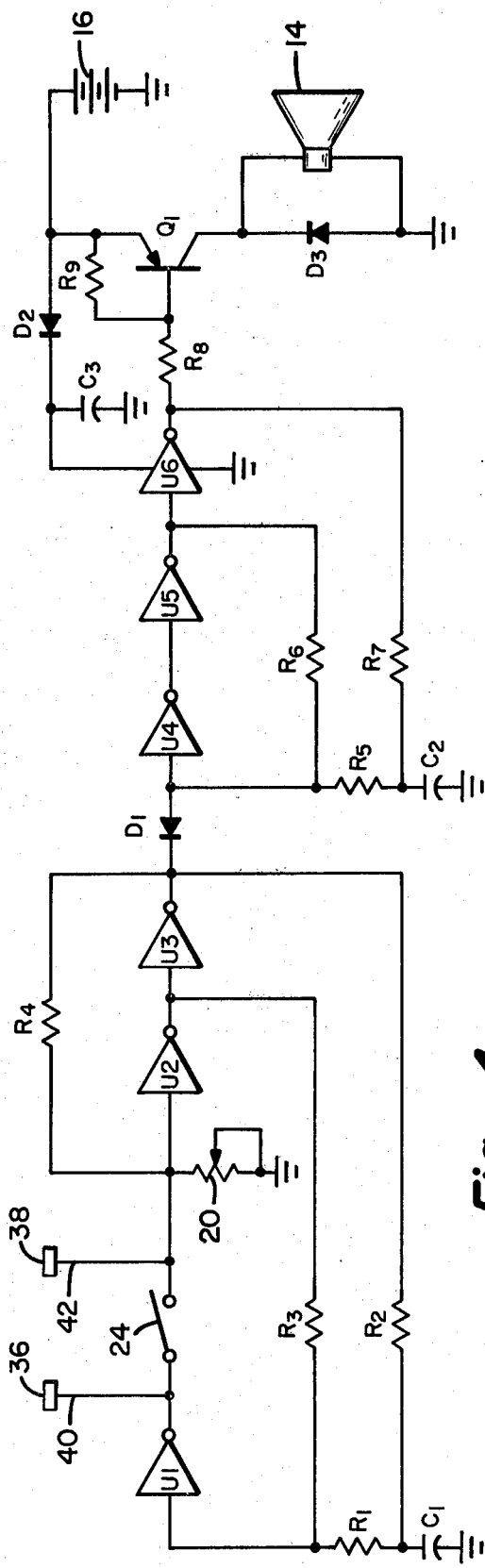
FIG. 4 is a schematic of the circuitry of the device.

FIG. 4 is a detailed schematic of the device. The test switch is placed in parallel with the electrodes 36 and 38 so that a conductive path is placed between the output terminal of inverter U1 and the input terminal of inverter U2. Since the test switch 24 is a normally open switch, closing the switch or providing a low resistance path between electrodes 36 and 38 completes the signal path from the output of inverter U1 to the input of inverter U2. The output of inverter U2 is connected to the input of inverter U1 through resistor R3 and to the input of inverter U3. The output of inverter U3 is connected to U4 the input of inverter U2 and through resistor R2 to the point of connection of the series combination of resistor R1 and capacitor C1, which is connected between the input of inverter U1 and ground.

The output of inverter U3 is connected to the cathode of the diode D1, the anode of which is connected to the input of inverter U4. The output of inverter U4 is connected to the input of inverter U5, the output of which is connected through resistor R6 to the input of inverter U4.

The output of inverter U5 is also connected to the input of inverter U6, the output of which is connected through resistor R7 to the point of connection of the series connection of resistor R5 and capacitor C2 connected between the input of inverter U4 and ground. Inverter U6 is shown as connected to battery 16 through a forward biased diode D2. As indicated in the list of components below, the inverters U1 through U6 are all mounted on a single chip powered by battery 16, hence the indication of only a single power line and ground to inverter U6. Capacitor C3 serves to decouple the inverters U1 through U6 from the power supply.

An output transistor Q1 has its emmiter connected to the battery 16, its base connected through resistor R8 to the output of inverter U6, and a base emmiter resistor R9 connected between its emmiter and base. The collector of transistor Q1 is connected to drive speaker 14 which has a flyback diode D3 connected across its winding to minimize inductive switching transients as the speaker is driven by transistor Q1.

The circuit of FIG. 4 operates as follows.

When the test switch S1 is open, the output of U3 is low. The output is fed back through R4 to the input of U2 which is also low. The output of U2 is high, as is the input of U3. U1 has a high output while its input is low.

Closure of the test switch 24 or presence of a low impedance path between electrodes 36 and 38 connects the initial high voltage at the output of U1 to the input of U2. The output of U2 switches to a zero and the output of U3 switches to a one, commencing to charge capacitor C1 at a charging rate determined by the RC time constant of R2 and C1. The output of U1 will switch from a one to a zero when the voltage at its input reaches a threshold level. After U1 switches its output switches to a zero, the output of U2 switches to a one, and the output of U3 switches to a zero. The circuit remains in this condition until the voltage at the input of U1 decreases to less than the threshold value and U1 switches again to repeat the above sequence. Use of the component values listed at the end of the specification results in an oscillator circuit involving U1, U2, and U3, which has a frequency of approximately 5 Hz.

The 5 Hz oscillator of U1, U2, and U3 turns on and off a 2.5 K Hz oscillator made up of inverters U4, U5, and U6, which operates at 2.5 K Hz in the same manner that the 5 Hz oscillator operates. The output of U6 is, therefore, an alternating series of 2.5 K Hz square waves turned on and off at a 5 Hz rate.

Thus, the circuit of FIG. 4 operates as a free running, or astable, multivibrator, which is intermittently gated by another astable multivibrator at a much lower frequency.

The output signal of the 2400 Hz oscillator is driven through resistor R8 to the base of PNP transistor Q1. Q1 has a base emitter resistor R9, and has its collector connected to one terminal of an audio transducer 14, which has a back biased diode D2 connected across the terminals thereof.

The power to the circuit is supplied by three or four 1.5 volt watch batteries. The diode D2 and capacitor C3 provide a filter on the DC supply provided to the buffer amplifier chip to prevent battery voltage fluctuations from affecting the operation of the buffer amplifiers and the astable multivibrators.

From the above, it is apparent that the present invention provides a self-contained wearable device for use by diabetics to provide an audible indication of the onset of insulin shock. It has been found advantageous to construct the embodiment illustrated using components having the values specified within the description or as given in the following table:

| Resistors | Ohms |
|---|---|
| R1, R2, R5, R7 | 3M |
| R3, R6 | 22M |
| R4 | 10M |
| R8, R9 | 2.7K |
| 20 | 2M adjustable |
| Capacitors | Farads |
| C1 | .1 micro |
| C2 | 50 pico |
| C3 | 10 micro |
| diodes D1, D2 | 1N4148 |
| U1–U6 | CD4049 B Hex Inverter |

| -continued | |
|---|---|
| Q1 | 2N4403 |

It is therefore to be understood that, within the scope of the appended claims, the invention may be practiced otherwise than is specifically described.

I claim:

1. Apparatus for detecting the onset of insulin shock in a diabetic wherein the apparatus is contained in a wrist watch type case constructed and arranged for attachment to the wrist of the wearer, said case including a pair of apertures on the back face thereof, said apparatus comprising, in combination:

sensor means including a pair of electrodes mounted on a substrate enclosed within the case of the apparatus and positioned with said electrodes aligned within said apertures and insulated from each other and said case, the position of said substrate being variable to permit adjustment of the distance between said electrodes and the skin of the wearer;

detector means connected to said sensor means for providing an output when the amount of perspiration on the skin of the wearer exceeds a threshold level; and annunciator means connected to said detector means to receive the output therefrom and provide an audible output indication.

2. Apparatus contained in a wrist watch type case constructed and arranged for attachment to the wrist of a diabetic for detecting the onset of insulin shock comprising, in combination:

sensor means constructed and arranged for application to the skin of the wearer; said sensor means comprising a pair of planar electrodes mounted on the back of the case of the apparatus and insulated from each other and said case, said electrodes also being recessed into the back of said case, whereby said case when attached to the arm of the wearer does not bring said electrodes into direct contact with the skin of the wearer, and further whereby said electrodes come into direct contact with perspiration forming on the skin of said wearer in the event of the onset of insulin shock;

detector means connected to said sensor means for providing an output indicative of the onset of insulin shock when the electrodes come into contact with perspiration on the skin of the wearer; and annunciator means connected to said detector means for receiving the output therefrom and providing an audible output indication of the onset of insulin shock.

3. The invention of claim 2 or 1 wherein said detector means comprises an audio oscillator normally operating on a quiescent mode and switched to an oscillating mode in the response to a change in the resistance between said sensor means.

4. The invention of claim 3 wherein the output of said audio oscillator at a first frequency is itself turned on and off at a lower frequency to provide a more pronounced audible indication.

5. The invention of claim 4 wherein the first frequency is approximately 2500 Hz and the lower frequency at which the first frequency is modulated is approximately 5 Hz.

* * * * *